US011008531B2

(12) United States Patent
Lamprecht et al.

(10) Patent No.: US 11,008,531 B2
(45) Date of Patent: May 18, 2021

(54) METHODS OF REFINING A GRAIN OIL COMPOSITION TO MAKE ONE OR MORE GRAIN OIL PRODUCTS, AND RELATED SYSTEMS

(71) Applicant: POET Research, Inc., Sioux Falls, SD (US)

(72) Inventors: Benjamin A. Lamprecht, Lennox, SD (US); Tyler L. Jordison, Brandon, SD (US); Alex T. McCurdy, Sioux Falls, SD (US); Steven T. Bly, Sioux Falls, SD (US)

(73) Assignee: POET RESEARCH, INC., Sioux Falls, SD (US)

( * ) Notice: Subject to any disclaimer, the term of this patent is extended or adjusted under 35 U.S.C. 154(b) by 0 days.

(21) Appl. No.: 16/880,172

(22) Filed: May 21, 2020

(65) Prior Publication Data
US 2020/0339910 A1   Oct. 29, 2020

Related U.S. Application Data

(63) Continuation of application No. 16/271,361, filed on Feb. 8, 2019, now Pat. No. 10,711,221.
(Continued)

(51) Int. Cl.
*C11B 3/00*    (2006.01)
*C11B 3/12*    (2006.01)
(Continued)

(52) U.S. Cl.
CPC ............... *C11B 3/006* (2013.01); *A23D 9/04* (2013.01); *C08L 95/00* (2013.01); *C10L 1/026* (2013.01);
(Continued)

(58) Field of Classification Search
CPC ... C11B 3/006; C11B 1/02; C11B 1/10; C11B 3/003; C11B 3/13; C10L 1/026;
(Continued)

(56) References Cited

U.S. PATENT DOCUMENTS 1,737,402 A   11/1929  Ayres, Jr. et al.
2,762,780 A    9/1956  Kulakow
(Continued)

FOREIGN PATENT DOCUMENTS

GB    481580 A    3/1938
GB    766394 A    1/1957
(Continued)

OTHER PUBLICATIONS

Leon Skaliotis, "Short Path to Premium Quality Oils", food Marketing & Technology, Feb. 2011, pp. 23-26, (4 pages).
(Continued)

*Primary Examiner* — Deborah D Carr
(74) *Attorney, Agent, or Firm* — Honigman LLP

(57) ABSTRACT

The present disclosure is related to refining one or more grain oil composition streams (e.g., distillers corn oil or syrup) in a biorefinery to provide one or more refined grain oil products, where each grain oil product has targeted amounts of a free fatty acid component and the fatty acid alkyl ester component.

24 Claims, 3 Drawing Sheets

Related U.S. Application Data

(60) Provisional application No. 62/628,380, filed on Feb. 9, 2018.

(51) Int. Cl.
| | |
|---|---|
| C10L 1/02 | (2006.01) |
| C08L 95/00 | (2006.01) |
| C11B 1/02 | (2006.01) |
| C11B 1/10 | (2006.01) |
| C12P 7/64 | (2006.01) |
| C12P 7/06 | (2006.01) |
| C10M 101/04 | (2006.01) |
| A23D 9/04 | (2006.01) |
| C10L 1/19 | (2006.01) |

(52) U.S. Cl.
CPC ........... *C10L 1/191* (2013.01); *C10M 101/04* (2013.01); *C11B 1/02* (2013.01); *C11B 1/10* (2013.01); *C11B 3/00* (2013.01); *C11B 3/003* (2013.01); *C11B 3/12* (2013.01); *C12P 7/06* (2013.01); *C12P 7/64* (2013.01); *C12P 7/649* (2013.01); *C12P 7/6409* (2013.01); *C08L 2555/64* (2013.01); *C10L 2200/0446* (2013.01); *C10L 2200/0476* (2013.01); *C10L 2200/0484* (2013.01); *C10L 2230/082* (2013.01); *C10L 2270/026* (2013.01); *C10L 2290/08* (2013.01); *C10L 2290/26* (2013.01); *C10L 2290/543* (2013.01); *C10L 2290/544* (2013.01); *C10L 2290/562* (2013.01); *C10M 2203/003* (2013.01)

(58) Field of Classification Search
CPC ........ C10L 1/191; A23D 9/04; C10M 101/04; C12P 7/06; C12P 7/64; C12P 7/6409; C12P 7/649
USPC ........................................................ 554/175
See application file for complete search history.

(56) References Cited

U.S. PATENT DOCUMENTS

| | | |
|---|---|---|
| 2,881,195 A | 4/1959 | Hayes et al. |
| 3,354,188 A | 11/1967 | Bock et al. |
| 4,049,686 A | 9/1977 | Ringers et al. |
| 4,609,500 A | 9/1986 | Strecker |
| 4,698,185 A | 10/1987 | Dijkstra et al. |
| 4,713,155 A | 12/1987 | Arutjunian et al. |
| 5,239,096 A | 8/1993 | Rohdenburg et al. |
| 5,512,691 A | 4/1996 | Barnicki et al. |
| 5,516,924 A | 5/1996 | van de Sande et al. |
| 6,015,915 A | 1/2000 | Jamil et al. |
| 6,033,706 A | 3/2000 | Silkeberg et al. |
| 6,103,918 A | 8/2000 | Dahlén |
| 6,407,271 B1 | 6/2002 | Deffense |
| 6,426,423 B1 | 7/2002 | Copeland et al. |
| 6,743,930 B2 | 6/2004 | Li |
| 6,844,458 B2 | 1/2005 | Copeland et al. |
| 6,924,381 B2 | 8/2005 | Dawson |
| 7,122,216 B2 | 10/2006 | Copeland et al. |
| 7,696,369 B2 | 4/2010 | Kellens et al. |
| 7,713,727 B2 | 5/2010 | Dayton et al. |
| 7,842,484 B2 | 11/2010 | Lewis |
| 7,879,917 B2 | 2/2011 | Cheng et al. |
| 7,893,115 B2 | 2/2011 | Cheng et al. |
| 7,919,291 B2 | 4/2011 | Lewis et al. |
| 8,008,516 B2 | 8/2011 | Cantrell et al. |
| 8,076,123 B2 | 12/2011 | Chou |
| 8,232,418 B1 | 7/2012 | Bilbie et al. |
| 8,435,766 B2 | 5/2013 | Kellens et al. |
| 8,702,819 B2 | 4/2014 | Bootsma |
| 8,962,059 B1 | 2/2015 | Froderman et al. |
| 9,045,712 B2 | 6/2015 | Dayton et al. |
| 9,061,987 B2 | 6/2015 | Bootsma |
| 9,109,179 B2 | 8/2015 | Cowin et al. |
| 9,144,758 B2 | 9/2015 | Wang et al. |
| 9,228,211 B2 | 1/2016 | Søe et al. |
| 9,255,239 B1 | 2/2016 | Wiese |
| 9,340,749 B1 | 5/2016 | Kozyuk et al. |
| 9,453,180 B2 | 9/2016 | Kozyuk et al. |
| 9,481,853 B2 | 11/2016 | Gordon et al. |
| 9,534,182 B1 | 1/2017 | Ballard |
| 9,556,399 B2 | 1/2017 | Kozyuk et al. |
| 9,695,449 B2 | 7/2017 | Bootsma |
| 9,896,643 B2 | 2/2018 | Redford |
| 9,961,916 B2 | 5/2018 | Arhancet et al. |
| 10,604,776 B2 | 3/2020 | McCurdy et al. |
| 10,815,430 B2 | 10/2020 | Gutierrez et al. |
| 10,815,506 B2 | 10/2020 | Rancke-Madsen et al. |
| 2006/0041152 A1 | 2/2006 | Cantrell et al. |
| 2008/0064889 A1 | 3/2008 | Palacios |
| 2008/0146851 A1 | 6/2008 | Schonemann et al. |
| 2009/0306419 A1 | 12/2009 | Myong et al. |
| 2010/0058649 A1 | 3/2010 | Bootsma |
| 2012/0245370 A1 | 9/2012 | Sheppard et al. |
| 2013/0109873 A1 | 5/2013 | Bootsma |
| 2015/0230488 A1 | 8/2015 | de Man et al. |
| 2015/0291923 A1 | 10/2015 | Bootsma |
| 2017/0066995 A1 | 3/2017 | Borst et al. |
| 2017/0107449 A1 | 4/2017 | Hruschka et al. |
| 2017/0107452 A1* | 4/2017 | Dasari ..................... C11B 3/006 |
| 2017/0283838 A1 | 10/2017 | Bootsma |
| 2018/0340067 A1 | 11/2018 | McCurdy et al. |
| 2018/0340068 A1 | 11/2018 | McCurdy et al. |
| 2018/0340197 A1 | 11/2018 | McCurdy et al. |
| 2019/0249109 A1 | 8/2019 | Lamprecht et al. |
| 2019/0376002 A1 | 12/2019 | Urban et al. |
| 2020/0063168 A1 | 2/2020 | Bootsma |
| 2020/0165642 A1 | 5/2020 | McCurdy et al. |
| 2020/0299610 A1 | 9/2020 | Marques De Lima |

FOREIGN PATENT DOCUMENTS

| | | | |
|---|---|---|---|
| GB | 1065720 A | 4/1967 | |
| GB | 1562380 A | 3/1980 | |
| WO | 9323508 A1 | 11/1993 | |
| WO | 9421762 A1 | 9/1994 | |
| WO | 9801518 A1 | 1/1998 | |
| WO | 2004007654 A1 | 1/2004 | |
| WO | WO-2004007654 * | 1/2004 | ............... A23D 9/00 |
| WO | 2010053244 A1 | 5/2010 | |
| WO | WO-2010053244 * | 5/2010 | ............... A23D 9/00 |
| WO | 2014037008 A1 | 3/2014 | |
| WO | WO-2014037008 * | 3/2014 | ............... C11B 7/00 |
| WO | 2014158011 A1 | 10/2014 | |
| WO | 2015168020 A2 | 11/2015 | |
| WO | WO-2015168020 * | 11/2015 | ............... C12P 7/06 |
| WO | 2015181308 A1 | 12/2015 | |
| WO | 2016003465 A1 | 1/2016 | |
| WO | 2016178676 A1 | 11/2016 | |
| WO | 2018024654 A1 | 2/2018 | |
| WO | 2018217198 A1 | 11/2018 | |
| WO | 2018218033 A2 | 11/2018 | |
| WO | 2019069992 A1 | 4/2019 | |

OTHER PUBLICATIONS

LCI Corporation, "Short Path Evaporation", retrieved from https://lcicorp.com/short_path_evaporators/short_path_evaporator, (2 pages).
Japir et al., "Separation of Free Fatty Acids from High Free Fatty Acid Crude Palm Oil Using Short-Path Distillation", The 2016 UKM FST Postgraduate Colloquium, AIP Conf. Proc. 1784, 030001-1-030001-8, 2016, (9 pages).
"Back-End Value Enhanced through Patented Technology and Strategic Partnerships" retrieved from WWW.Valicor.com, (5 pages).
International Search Report, for International Application No. PCT/US2019/017286, dated May 14, 2019 (6 pages).
"Micro-fine silica treated with an organic silicone compound", DUMACIL® 300 FGK, Elementis Specialties, Apr. 2017, 1 page.
"Micro-fine silica treated with an organic silicone compound", DUMACIL® 100 FGK, Elementis Specialties, Apr. 2017, 1 page.

(56) References Cited

OTHER PUBLICATIONS

"Standard Test Method for Foaming Properties of Surface-Active Agents1", Designation: D 1173-53, Reapproved 2001, 2 pages.
"Defoamer", Retrieved from 'https://en.wikipedia.org/wiki/Defoamer' on May 30, 2019, 5 pages.
Abdulkadir et al., "Production and Refining of Corn Oil from Hominy Feed a By-Product of Dehulling Operation", ARPN Journal of Engineering and Applied Sciences, vol. 6, No. 4, Apr. 2011, 7 pages.
"Corn Oil", Retrieved from 'https://corn.org/resources/?fwp_resource_type=pdf&fwp_search=Corn%20Oil', 2006, 24 pages.
International Search Report for International Application No. PCT/US2019/036578, dated Oct. 11, 2019, 5 pages.
Unpublished Utility U.S. Appl. No. 17/026,771, filed Sep. 21, 2020.
Unpublished Utility U.S. Appl. No. 17/063,009, filed Oct. 5, 2020.
Friedrich et al., "Properties and Processing of Corn Oils Obtained by Extraction With Supercritical Carbon Dioxide", JAOCS, vol. 61, No. 12, 1984, (3 pages).
Saini et al., "Carotenoid extraction methods: A review of recent developments", Food Chemistry, No. 240, pp. 90-103, 2018, (14 pages).

\* cited by examiner

METHODS OF REFINING A GRAIN OIL COMPOSITION TO MAKE ONE OR MORE GRAIN OIL PRODUCTS, AND RELATED SYSTEMS

CROSS REFERENCE TO RELATED APPLICATION

This application is a continuation patent application of non-provisional patent application Ser. No. 16/271,361 filed on Feb. 8, 2019, which claims the benefit of U.S. Provisional Patent Application Ser. No. 62/628,380, filed Feb. 9, 2018, wherein the entire disclosure of each of said patent applications is incorporated herein by reference.

FIELD

The present disclosure is related to refining one or more grain oil composition streams (e.g., distillers corn oil or syrup) in a biorefinery to provide one or more refined grain oil products, where each grain oil product has targeted amounts of a free fatty acid component and the fatty acid alkyl ester component.

BACKGROUND

The present disclosure relates to refining and recovering one or more grain oil products from a biorefinery that uses at least one or more grain feedstocks that can ultimately be used to convert sugar into one or more biochemicals.

Oil that is present in the grain feedstock can be recovered as a co-product. There is a continuing need to provide methods and systems to improve the profile of one or more chemical constituents in a grain oil product that is recovered as a co-product from a biorefinery.

SUMMARY

The present disclosure includes embodiments of a method of refining a grain oil composition to make one or more grain oil products. The method includes providing a grain oil composition, wherein the grain oil composition comprises a fatty acid alkyl ester component; and exposing the grain oil composition to temperature and pressure conditions for a time period to evaporate at least a portion of the fatty acid alkyl ester component from the grain oil composition to form a first grain oil product and a second oil product. The first grain oil product has a first concentration of fatty acid alkyl ester component and the second grain oil product has a second concentration of fatty acid alkyl ester component. The first concentration of fatty acid alkyl ester component is less than the second concentration of fatty acid alkyl ester component.

The present disclosure also includes embodiments a system for refining a grain oil composition to make one or more grain oil products. The system includes a system configured to provide a grain oil composition. The grain oil composition includes a fatty acid alkyl ester component. The system also includes a system configured to expose the grain oil composition to temperature and pressure conditions for a time period to evaporate at least a portion of the fatty acid alkyl ester component from the grain oil composition to form a first grain oil product and a second oil product. The first grain oil product has a first concentration of fatty acid alkyl ester component and the second grain oil product has a second concentration of fatty acid alkyl ester component. The first concentration of fatty acid alkyl ester component is less than the second concentration of fatty acid alkyl ester component.

DETAILED DESCRIPTION

Figure 1:
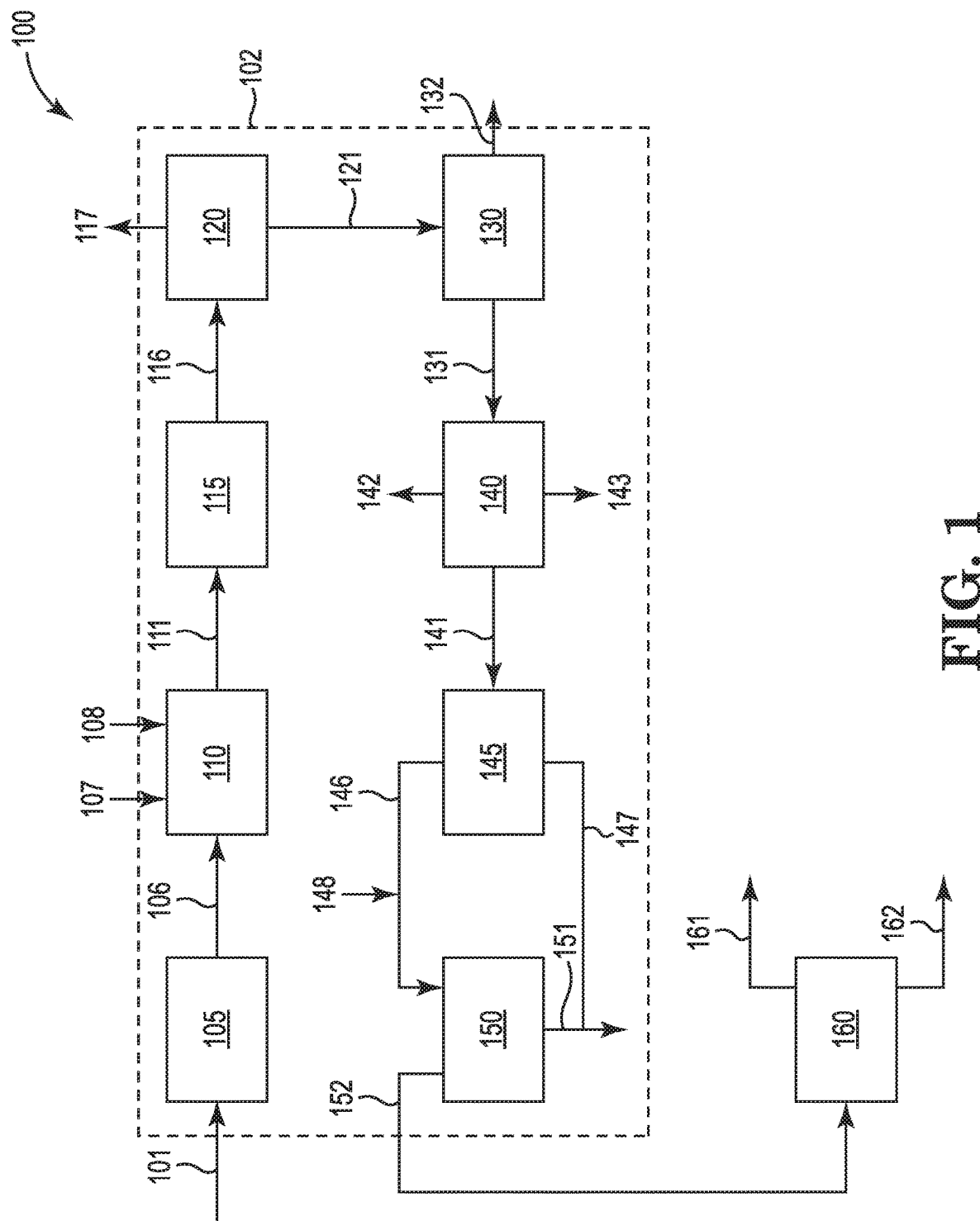
FIG. 1 is a schematic flow diagram of an embodiment of providing a grain oil composition according to the present disclosure.

As described in detail herein, the present disclosure includes embodiments of a method of refining a grain oil composition to make one or more grain oil products that have a variety of end uses.

As used herein, a "grain oil composition" refers to an oil composition that is obtained from a biorefinery that produces one or more biochemicals from one or more microorganisms (e.g., yeast) that convert monosaccharides derived from one or more polysaccharides in the grain. Oil present in the grain is present in ground grain material as it is processed in the biorefinery. A composition that includes the grain oil can be extracted from one or more points in the biorefinery so that the grain oil composition can be refined into a grain oil product according to the present disclosure. Examples of grains that can be used to make a grain oil composition include corn, soybean, combinations of these, and the like.

A grain oil composition that can be refined according to the present disclosure can have at least a moisture content, total solids content (suspended solids content plus dissolved solids content), free fatty acid component, and fatty acid alkyl ester content as described herein.

As used herein, "moisture content" refers to the amount of water in the grain oil composition. In some embodiments, a grain oil composition can have a moisture content of 20 percent or less based on the total weight of the grain oil composition, 10 percent or less based on the total weight of the grain oil composition, 5 percent or less based on the total weight of the grain oil composition, 2 percent or less based on the total weight of the grain oil composition, or even 1 percent or less based on the total weight of the grain oil composition. In some embodiments, a grain oil composition can have a moisture content in the range from 0.2 to 1.5 percent based on the total weight of the grain oil composition. Moisture content can be measured using near infrared spectroscopy (NIR) and according to ASTM E1064-12 Standard Method for Water in Organic Liquids by Coulometric Karl Fisher Titration.

As used herein, "total solids content" means the total content of dissolved and suspended solids based on the total weight of the grain oil composition. In some embodiments, a grain oil composition can have a total solids content in the range from 0 to 5 percent based on the total weight of the grain oil composition in some embodiments, a grain oil composition can have a suspended solids content of 5 percent or less based on the total weight of the grain oil composition, 2 percent or less based on the total weight of the grain oil composition, or even 1 percent or less based on the total weight of the grain oil composition (e.g., from 0.1 to 1 percent). In some embodiments, a grain oil composition can include a soap component (e.g., one or more sodium or potassium salts of fatty acids). For example, in some embodiments, a grain oil composition may include a soap component in an amount from 1 part per million (ppm) to 25,000 parts per million.

Before refining a grain oil composition according to the present disclosure, a grain oil composition can also include an amount of a free fatty acid (FFA) component and an amount of a fatty acid alkyl ester (FAAE) component. The level of FFA component and FAAE component in a grain oil composition can impact how it is subsequently used (discussed further below). Refining a grain oil composition according to the present disclosure can partition at least a portion of the FFA component and/or at least a portion of the FAAE component into two or more "grain oil products" (fractions) with different levels of the FFA component and/or FAAE component in each grain oil product depending on how a given grain oil product is to be used. As used herein a "free fatty acid" refers to an unesterified fatty acid, or more specifically, a fatty acid having a carboxylic acid head and a saturated or unsaturated unbranched aliphatic tail (group) of from 4 to 28 carbons. The term "aliphatic" has a generally recognized meaning and refers to a group containing only carbon and hydrogen atoms which is straight chain, branched chain, cyclic, saturated or unsaturated but not aromatic. A free fatty acid component includes one or more free fatty acids. Nonlimiting examples of free fatty acids include, e.g., caproic acid, capric acid, caprylic acid, lauric acid, myristic acid, palmitic acid, stearic acid, oleic acid, linolenic acid, linoleic acid, arachidic acid, and mixtures thereof.

In some embodiments, before refining a grain oil composition according to the present disclosure the grain oil composition can include a free fatty acid component present in an amount from 0 to 99 percent by weight based on the total weight of the grain oil composition. In some embodiments, before refining a grain oil composition according to the present disclosure the grain oil composition can include a free fatty acid component present in an amount of 15 percent or less by weight based on the total weight of the grain oil composition. In some embodiments, the free fatty acid component is present in an amount in the range from 0.1 to 15 percent by weight based on the total weight of the grain oil composition, from 0.5 to 9 percent by weight based on the total weight of the grain oil composition, or even from 5.0 to 9.0 percent by weight based on the total weight of the grain oil composition.

A fatty acid alkyl ester such as fatty acid ethyl ester (FAEE) is an esterified (not free) fatty acid. For example, FAEE is a fatty acid esterified with ethanol as a free fatty acid becomes exposed to ethanol during fermentation and through distillation in a biorefinery. A fatty acid alkyl ester component includes one or more fatty acid alkyl esters. Nonlimiting examples of fatty acid ethyl esters include ethyl palmitate, ethyl stearate, ethyl oleate, ethyl linoleate, and ethyl linolenate, and mixtures thereof.

In some embodiments, before refining a grain oil composition according to the present disclosure the grain oil composition can include a fatty acid alkyl ester component present in an amount from greater than 0 to 99 percent based on the total weight of the grain oil composition. In some embodiments, before refining a grain oil composition according to the present disclosure the grain oil composition can include a fatty acid alkyl ester component present in an amount of at least 5 percent by weight based on the total weight of the grain oil composition, at least 6 percent by weight based on the total weight of the grain oil composition, at least 15 percent by weight based on the total weight of the grain oil composition, at least 30 percent by weight based on the total weight of the grain oil composition, at least 40 percent by weight based on the total weight of the grain oil composition, at least 50 percent by weight based on the total weight of the grain oil composition, at least 60 percent by weight based on the total weight of the grain oil composition, or even at least 70 percent by weight based on the total weight of the grain oil composition. In some embodiments, the fatty acid alkyl ester component is present in an amount in the range from 5 to 90 percent by weight based on the total weight of the grain oil composition, in the range from 6 to 90 percent by weight based on the total weight of the grain oil composition, in the range from 6.5 to 90 percent by weight based on the total weight of the grain oil composition, or even in the range from 7 to 60 percent by weight based on the total weight of the grain oil composition.

The FFA component and the FAAE component can be generated due to the grain oil being exposed to one or more processes in a biorefinery. For instance, the amount of free fatty acids that are generated can be increased as the temperature increases. An example of generating free fatty acids due to an elevated temperature includes biorefineries that cook corn mash in jet cookers at temperatures of 200° F. or higher. Another example of generating free fatty acids due to an elevated temperature includes exposing a fermentation beer to a distillation temperature to recover a biochemical such as ethanol. In some embodiments, such a distillation temperature can be in the range from 180° F. to 210° F.

The present inventors have found that FAEE are most likely to be generated in the presence of one or more catalysts such as esterases and/or lipases. Accordingly, in saccharification processes that avoid high temperatures (e.g., 200° F. and greater) associated with jet cooking corn mash, endogenous esterases and lipases found in grain (e.g., corn) can avoid being denatured to an undue degree so that they remain viable and available during fermentation to generate relatively high levels of FAEE in the presence of ethanol. An example of a saccharification process that occurs at relatively low temperatures as compared to jet-cooking is described in U.S. Pat. No. 7,842,484 (Lewis), wherein the entirety of said patent document is incorporated herein by reference.

Alternatively, or in addition to endogenous esterase enzymes, one or more exogenous esterase enzymes can be added at one or more points in a fermentation process so that they are present during fermentation to generate even more FAEE.

An example of adding exogenous esterase enzyme is described in U.S. Pub. No.: 2018/0340197 (McCurdy et al.), wherein the entirety of said patent publication is incorporated herein by reference.

Additional, nonlimiting examples of grain oil compositions that can be refined according to the present disclosure are also described in U.S. Pat. No. 8,702,819 (Bootsma); U.S. Pat. No. 9,061,987 (Bootsma); U.S. Pat. No. 9,695,449 (Bootsma); U.S. Publication No. US 2013/0109873 A1 (Bootsma); U.S. Publication No. US 2015/0291923 A1 (Bootsma); U.S. Publication No. US 2017/0283838 A1 (Bootsma); U.S. Publication No. US 2018/0340068 A1 (McCurdy et al.); U.S. Publication No. US 2018/0340197 A1 (McCurdy et al.); and WO Publication No. WO 2018/217198 A1 (McCurdy et al.), wherein the entirety of each patent and published patent application is incorporated herein by reference.

An example of providing a grain oil composition for further refinement is described with respect to FIG. 1. FIG. 1 shows a process 100 that includes a system 160 coupled with a biorefinery 102 to refine a grain oil composition produced in the biorefinery 102. As shown in FIG. 1, biorefinery 102 can grind whole grain 101 (e.g., corn) that is fed to grinding system 105 to form whole ground grain 106. The whole ground grain 106 includes grain oil and one or more polysaccharides (e.g. starch). After grinding, the whole ground grain 106 can be combined with an aqueous process stream 107 (e.g., fresh water, recycled process water, combinations of these, and the like) and one or more exogenous enzymes 108 in a saccharification system 110 to form a slurry and convert at least a portion of the one or more polysaccharides into one or more monosaccharides to form a saccharification broth 111.

Nonlimiting examples of one or more saccharification enzymes 108 include an amylase, such as an alpha amylase (e.g., acid fungal amylase) and/or a glucoamylase.

Saccharification can be operated at a pH and temperature to facilitate converting at least a portion of the one or more polysaccharides into one or more monosaccharides to form a saccharification broth 111. In some embodiments, the pH during saccharification can be from 3.0 to 6.0, from 3.5 to 6.0, from 4.0 to 5.0, from 4.0 to 4.5, or even from 4.5 to 5.0. In some embodiments, the temperature during saccharification can be from 25° C. to 40° C., or even from 30° C. to 35° C.

After saccharification, the saccharification broth 111 can be exposed to fermentation conditions 115 to ferment at least a portion of the one or more monosaccharides in the saccharification broth to form a fermentation beer 116. The fermentation beer 116 includes, e.g., grain oil and a biochemical (e.g., alcohol such as ethanol). Fermentation beer can include other components such as solids (dissolved solids and suspended solids) and water. As mentioned above, if desired, one or more exogenous esterase enzymes can be present during fermentation to increase the esterification of one or more fatty acids with alcohol that is produced during fermentation. In some embodiments, one or more esterase enzymes include one or more exogenous lipase enzymes. The amount of one or more esterase exogenous esterase enzymes added to a fermentation mash before or during fermentation can be selected based on the amount of oil determined (e.g., calculated) to be present in the whole grain 101 (e.g., corn) that is fed to grinding system 105. In some embodiments, the amount of esterase may be from about 0.001% to about 25% w/w of grain oil, e.g., about 0.01% to about 20% w/w of grain oil, e.g., from about 0.02% to about 0.2% w/w of grain oil, about 0.04% to about 4% w/w of grain oil, about 2% to about 20% w/w of grain oil, or about 0.03% to about 0.5 w/w of grain oil.

The pH during fermentation can also influence the FAAE (e.g., FAEE) content that is ultimately recovered in the grain oil composition. For example, a higher pH during ethanol fermentation can result in a higher FAEE component content while still being suitable for the microorganism to convert monosaccharide into ethanol.

Alternatively, process 100 can be carried out with simultaneous saccharification and fermentation (SSF). For example, in a low temperature, no-cook SSF process, saccharification and fermentation can be carried out at a temperature in the range from 40 to 95° F., or even 65 to 95° F. Such an SSF process can be performed over a time period of 18 to 120 hours, or even 48 to 120 hours. Such an SSF process can be performed at a pH of 4 to 7, or even 4 to 6. An example of SSF is described in U. S. Pat. No. 7,842,484 (Lewis), wherein the entirety of said patent document is incorporated herein by reference.

After fermentation, ethanol 117 can be separated from and recovered from the fermentation beer 116 in distillation system 120. In some embodiments, the highest temperature that the grain oil is exposed to in an ethanol process occurs in distillation. In some embodiments, a grain oil composition may be recovered without being exposed to a temperature of 200° F. or greater, or even 190° F. or greater. Because grain oil composition has not been exposed to such temperature conditions, the grain oil composition can have relatively low levels of FFA and relatively high levels of FAAE (e.g., FAEE) as compared to a grain oil composition that has been through jet cooking of corn mash (described above).

Whole stillage 121 from the distillation system 120 can be separated into thin stillage 131 and wet cake 132 in separation system 130 (e.g., one or more decanters).

Wet cake 132 can be used to form one or more of Wet Distillers Grain (WDG), Dried Distillers Grain (DDG), and Dried Distillers Grain with Soluble (DDGS).

Thin stillage 131 can be concentrated in concentrating system 140 by removing at least a portion of water 142. Water 142 can be removed thermally (e.g., one or more evaporators) and/or mechanically (e.g., via one or more centrifuges such as one or more two-phase and/or three-phase disk stack centrifuges in series and/or parallel) and form a syrup 141. Water stream (process water stream) can be used at one or more points in process 100 such as "backset" in system 110.

Optionally, at least a portion of solids 143 can also be separated from thin stillage via system 140 (e.g., via one or more centrifuges such as one or more two-phase and/or three-phase disk stack centrifuges in series and/or parallel).

The syrup 141 can be separated into an oil/water emulsion 146 and aqueous stream 147 via separation system 145 (e.g., via one or more centrifuges such as one or more two-phase and/or three-phase disk stack centrifuges in series and/or parallel). The oil/water emulsion 146 can have its pH adjusted if desired to facilitate "breaking" the emulsion. For example, a caustic 148 such as sodium hydroxide can be added to emulsion 146 to raise the pH of oil/water emulsion 146.

Separation system 150 can separate stream 146 into an aqueous stream 151 and a grain oil composition 152. The grain oil composition 152 can be further refined as described herein. An example of separation system 150 includes one or more centrifuges such as one or more two-phase and/or three-phase disk stack centrifuges in series and/or parallel.

Further, the pH adjustment of oil/water emulsion 146 can affect the amount of free fatty acids that are separated from oil/water emulsion 146 into aqueous stream 151 by saponifying the fatty acids thus making them more water soluble. Thus, the amount of the free fatty acids that are removed can be adjusted based on the pH adjustment of oil/water emulsion 146. For example, as the pH of emulsion 146 is increased a grain oil composition 152 can be formed that includes relatively lower levels of free fatty acids. In some embodiments, the pH of oil/water emulsion can be adjusted to a pH from 7.5 to 10, or even from 8 to 10.

According to the present disclosure, a grain oil composition can be refined to provide one or more grain oil products having target profiles of FFA and/or FAAE for one or more end-uses. Embodiments of the present disclosure include exposing the grain oil composition to temperature and pressure conditions for a time period to evaporate at least a portion of the free fatty acid component and the fatty acid alkyl ester component from the grain oil composition to form a first grain oil product and a second oil product.

Figure 2:
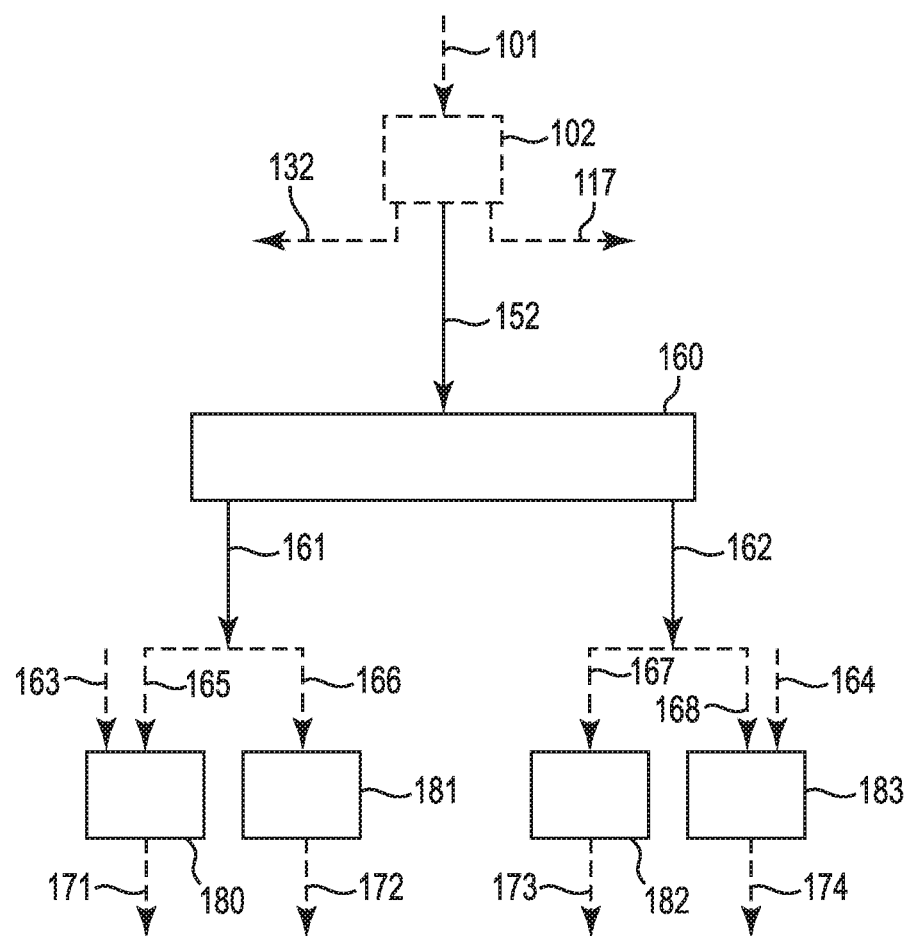
FIG. 2 is a schematic flow diagram illustrating using short path evaporation in an embodiment according to the present disclosure.

A nonlimiting example of refining a grain oil composition according to the present disclosure is illustrated in FIG. 2 with respect to system 160. FIG. 2 shows an illustrative embodiment incorporating system 160 into a corn ethanol biorefinery 102. The same reference characters used in FIG. 1 are used to illustrate similar features in FIG. 2 so their description is not repeated.

System 160 can include an apparatus adapted or configured to expose the grain oil composition 152 to temperature and pressure conditions by feeding the grain oil composition 152 to the apparatus in a manner that permits at least a portion of the free fatty acid component and the fatty acid alkyl ester component to be evaporated and then condensed to form and recover second grain oil product 161. System 160 can also be adapted or configured to expose the grain oil composition 152 to temperature and pressure conditions for a relatively short time period, as described below, such that at least a portion (e.g., substantially all of) the grain oil composition is exposed to the temperature and pressure of system 160 for a time period to permit at least a portion of the free fatty acid component and the fatty acid alkyl ester component to be evaporated from the grain oil composition 152 and then condensed to form and recover second grain oil product 161.

One example of a system 160 is a short path evaporator (also referred to as a molecular distillation system). Other examples of system 160 can include high vacuum distillation systems referred to as wiped-film evaporator, centrifugal molecular distillation, or falling film evaporator, which are described in U.S. Pat. No. 5,512,691 (Barnicki et al.), wherein the entirety of said patent is incorporated herein by reference.

Figure 3:
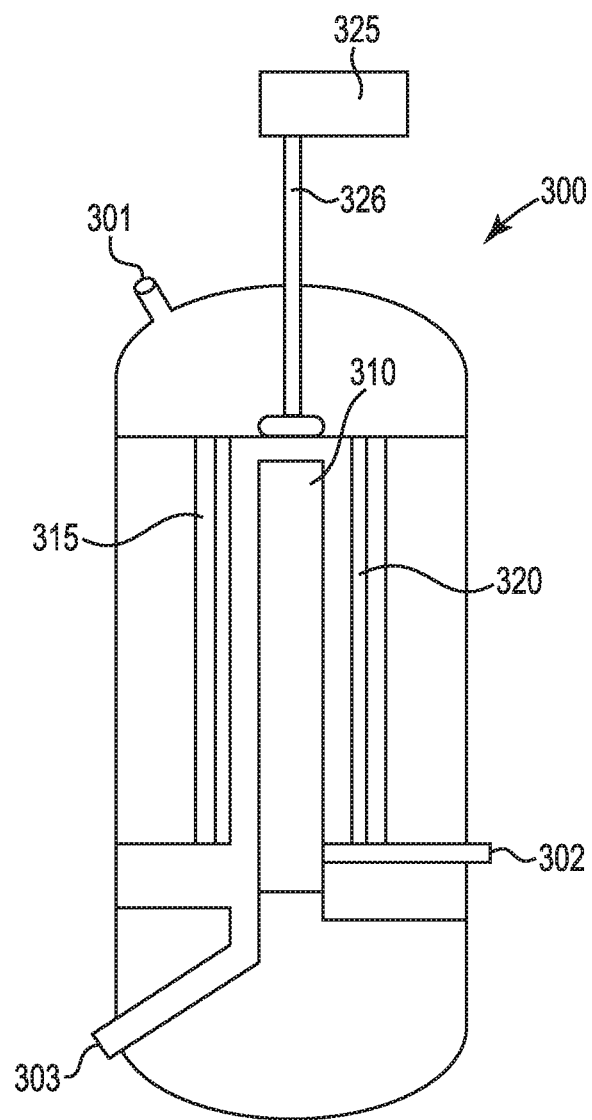
FIG. 3 is a cross-section of one embodiment of a short path evaporator apparatus.

FIG. 3 shows a cross-section illustration of an exemplary short path evaporator 300. As shown, evaporator 300 includes an inlet 301 to receive grain oil composition 152. The grain oil composition 152 can flow and be distributed along the inner sidewall of shell 315 so that the grain oil composition can flow down the shell 315 and form a film. One or more sources of heat and vacuum can be coupled to the evaporator 300 so as to expose the grain oil composition 152 to temperature and pressure conditions as described herein as the grain oil composition 152 flows down shell 315.

A wiper mechanism 320 can be rotatably coupled to and driven by drive 325. Wiper mechanism 320 can facilitate forming a film along shell 315 for a given flow rate of grain oil composition 152 so that the grain oil composition can be heated in a short time period as described herein. As the grain oil composition 152 flows down shell 315, at least a portion of the FFA and FAEE components can vaporize and condense via internal condenser 310 and flow out of evaporator 300 as condensate 302 (overs). The remaining residue (bottoms) that does not vaporize and condense can flow out of evaporator 300 via outlet 303.

Returning to FIG. 2, the grain oil composition 152 can be exposed to temperature and pressure conditions for a time period in system 160 to evaporate at least a portion of the free fatty acid component and the fatty acid alkyl ester component from the grain oil composition 152 to form a first grain oil product (bottoms) 162 and a second grain oil product (distillate) 161. In some embodiments, the grain oil composition 152 can be exposed to a temperature in the range from 300 to 500° F., or even from 300 to 400° F. In some embodiments, the grain oil composition 152 can be exposed to a pressure in the range from 10 to 5000 millitorr, or even from 10 to 1000 millitorr. In some embodiments, the grain oil composition 152 can be exposed to such temperatures and/or pressures for a time period in the range from 1 second to 60 minutes, from 1 second to 30 minutes, from 1 second to 15 minutes, from 1 second to 10 minutes, from 1 second to 5 minutes, or even from 1 second to 30 seconds.

In some embodiments, the first grain oil product ("unders" or "bottoms") 162 includes a free fatty acid component present in an amount in the range from 0.5 to 10 percent by weight based on the total weight of the first grain oil product 162, or even from 1 to 5 percent by weight based on the total weight of the first grain oil product 162. In some embodiments, the first grain oil product 162 includes a fatty acid alkyl ester component present in an amount in the range from 0.5 to 5 percent by weight based on the total weight of the first grain oil product 162, or even from 1 to 3 percent by weight based on the total weight of the first grain oil product 162. In some embodiments, the second grain oil product ("distillate" or "overs") 161 includes a free fatty acid component present in an amount in the range from 5 to 55 percent by weight based on the total weight of the second grain oil product 161, from 11 to 50 percent by weight based on the total weight of the second grain oil product 161, or even from 15 to 45 percent by weight based on the total weight of the second grain oil product 161. In some embodiments, the second grain oil product 161 includes a fatty acid alkyl ester component present in an amount in the range from 20 to 99 percent by weight based on the total weight of the second grain oil product 161, from 45 to 95 percent by weight based on the total weight of the second grain oil product 161, or even from 50 to 90 percent by weight based on the total weight of the second grain oil product 161.

The first grain oil product 162 and second grain oil product 161 have a wide variety of end uses. Non-limiting end-uses of first grain oil product 162 include one or more of food grade (FG) oil, biodiesel, defoamer, bio-based lubricant, and emulsifier. For example, as shown in FIG. 2, in some embodiments at least a portion 167 of the first grain oil product 162 can be subjected to an upgrading process 182, as desired, to make a food grade (FG) oil 173. An example of an"upgrading" process includes refining at least a portion of first grain oil product 162 via deodorizing, winterizing, bleaching and/or refining. For example, refining may include adding a caustic to saponify FFA with subsequent removal of the soaps by filtration and/or centrifugation. Refining may also include adding an acid to precipitate gums with subsequent removal of the precipitate by filtration and/or centrifugation. As another example, at least a portion 168 of first grain oil product 162 can be used as a feedstock for making biodiesel 174 from a biodiesel plant 183, e.g. via chemical (e.g., alkali-catalysis) and/or enzymatic (e.g., lipase) transesterification. If desired, methanol 164 can be used to make the biodiesel 174.

Optionally, the first grain oil product 162 could be blended with one or more different oil compositions to adjust the compositional profile of grain oil product 162 based on a given end-use specification. Nonlimiting sources of such different oil compositions include grain oil composition 152, overs 161, and/or an oil from another process or facility that has a different amount (or none) of FAEE.

Non-limiting end-uses of second grain oil product 161 include one or more of "true" diesel, asphalt additive, defoamer, rubber additive, and ultra-low sulfur diesel (bunker fuel). For example, as shown in FIG. 2, in some embodiments, at least a portion 166 of the second grain oil product 161 can be used to make diesel 172 via catalytic cracking 181. Additionally, at least a portion 165 of the second grain oil product 161 can be used as an asphalt additive 171, e.g., as a softener, binder, viscosity reduction agent, rejuvenator and/or to increase its resistance to aging and cracking.

Optionally, the second grain oil product 161 could be blended with one or more different oil compositions to adjust the compositional profile of grain oil product 161 based on a given end-use specification. Nonlimiting sources of such different oil compositions include grain oil composition 152, unders 162, and/or an oil from another process or facility that has a relatively lower amount (or none) of FAEE. As an example, as shown in FIG. 2, the portion 165 of second grain oil product 161 could be blended with one or more other components 163 to make asphalt additive 171. For example, 163 could include other oil compositions (e.g., a fraction of grain oil composition 152, unders 162, and/or an oil from another process or facility that has a relatively lower amount (or none) of FAEE) to adjust the compositional profile of additive 171 based on a given specification.

What is claimed is:

1. A method of refining a grain oil composition to make one or more grain oil products, the method comprising:
   a) providing a grain oil composition obtained from a biorefinery, wherein the grain oil composition comprises a free fatty acid component present in an amount of 15 percent or less by weight based on the total weight of the grain oil composition, and wherein the grain oil composition comprises a fatty acid alkyl ester component present in an amount of at least 5 percent by weight based on the total weight of the grain oil composition; and
   b) exposing the grain oil composition to temperature and pressure conditions for a time period to evaporate at least a portion of the free fatty acid component from the grain oil composition to form a first grain oil product and a second grain oil product, wherein the first grain oil product has a first concentration of free fatty acid component and the second grain oil product has a second concentration of free fatty acid component, and wherein first concentration of free fatty acid component is less than the second concentration of free fatty acid component.

2. The method of claim 1, wherein the grain oil composition is provided by:
   a) separating thin stillage or syrup derived from thin stillage into an oil/water emulsion and a first aqueous stream;
   b) breaking the oil/water emulsion to break the emulsion to form a mixture; and
   f) separating the mixture into a second aqueous stream and the grain oil composition.

3. The method of claim 2, wherein breaking the oil/water emulsion comprises adjusting the pH of the oil/water emulsion to break the emulsion.

4. A defoamer comprising the first grain oil product of claim 1.

5. A method of making biodiesel, wherein the method comprises mixing the first grain oil product of claim 1 with methanol to make biodiesel.

6. The method of claim 5, further comprising mixing the first grain oil product with methanol in the presence of a catalyst to make biodiesel.

7. A method of making diesel, wherein the method comprises using the second grain oil product of claim 1 as a feedstock to make diesel via catalytic cracking.

8. The method of claim 1, wherein the fatty acid alkyl ester component is formed in the biorefinery via one or more enzymes chosen from lipase, esterase, and combinations thereof, wherein the one or more enzymes are endogenous enzymes and/or exogenous enzymes.

9. A method of refining a grain oil composition to make one or more grain oil products, the method comprising:
   a) providing a grain oil composition obtained from a biorefinery, wherein the grain oil composition comprises a fatty acid alkyl ester component present in an amount of at least 6 percent by weight based on the total weight of the grain oil composition; and
   b) exposing the grain oil composition to temperature and pressure conditions for a time period to evaporate at least a portion of the fatty acid alkyl ester component from the grain oil composition to form a first grain oil product and a second grain oil product, wherein the first grain oil product has a first concentration of fatty acid alkyl ester component and the second grain oil product has a second concentration of fatty acid alkyl ester component, and wherein the first concentration of fatty acid alkyl ester component is less than the second concentration of fatty acid alkyl ester component.

10. The method of claim 9, wherein the grain oil composition is provided by:
    a) separating thin stillage or syrup derived from thin stillage into an oil/water emulsion and a first aqueous stream;
    b) breaking the oil/water emulsion to break the emulsion to form a mixture; and
    f) separating the mixture into a second aqueous stream and the grain oil composition.

11. The method of claim 10, wherein breaking the oil/water emulsion comprises adjusting the pH of the oil/water emulsion to break the emulsion.

12. A method of making biodiesel, wherein the method comprises mixing the first grain oil product of claim 9 with methanol to make biodiesel.

13. The method of claim 12, further comprising mixing the first grain oil product with methanol in the presence of a catalyst to make biodiesel.

14. A method of refining a grain oil composition to make one or more grain oil products, the method comprising:
    a) providing a grain oil composition obtained from a biorefinery, wherein the grain oil composition has a fatty acid alkyl ester component having a first fatty acid alkyl ester component concentration;
    b) exposing the grain oil composition to temperature and pressure conditions for a time period to evaporate at least a portion of the fatty acid alkyl ester component from the grain oil composition to form a first grain oil product and a second grain oil product, wherein the grain oil composition that does not evaporate while exposing the grain oil composition to the temperature and the pressure conditions is the first grain oil product, wherein the first grain oil product has a second fatty acid alkyl ester component concentration that is less than the first fatty acid alkyl ester component concentration of the grain oil composition, and wherein the first grain oil product is a feedstock to make a final product chosen from defoamer, biodiesel, and combinations thereof.

15. The method of claim 14, wherein the fatty acid alkyl ester component is formed in the biorefinery via one or more enzymes chosen from lipase, esterase, and combinations thereof, wherein the one or more enzymes are endogenous enzymes and/or exogenous enzymes.

16. The method of claim 14, wherein the grain oil composition further comprises a free fatty acid component present in an amount of 15 percent or less by weight based on the total weight of the grain oil composition.

17. The method of claim 14, further comprising condensing evaporated fatty acid alkyl ester component to form a second grain oil product, wherein the second grain oil product has a third fatty acid alkyl ester component concentration that is greater than the first fatty acid alkyl ester component concentration of the grain oil composition, and wherein the second grain oil product is a feedstock to make a final product chosen from diesel via catalytic cracking, defoamer, ultra-low sulfur diesel, asphalt additive, and combinations thereof.

18. A method of refining a grain oil composition to make one or more grain oil products, the method comprising:
 a) providing a grain oil composition obtained from a biorefinery, wherein the grain oil composition has a fatty acid alkyl ester component having a first fatty acid alkyl ester component concentration;
 b) exposing the grain oil composition to temperature and pressure conditions for a time period to evaporate at least a portion of the fatty acid alkyl ester component from the grain oil composition to form a first grain oil product and a second grain oil product;
 c) condensing evaporated fatty acid alkyl ester component to form the second grain oil product, wherein the second grain oil product has a second fatty acid alkyl ester component concentration that is greater than the first fatty acid alkyl ester component concentration of the grain oil composition, and wherein the second grain oil product is a feedstock to make a final product chosen from diesel via catalytic cracking, defoamer, ultra-low sulfur diesel, asphalt additive, and combinations thereof.

19. The method of claim 18, wherein the fatty acid alkyl ester component is formed in the biorefinery via one or more enzymes chosen from lipase, esterase, and combinations thereof, wherein the one or more enzymes are endogenous enzymes.

20. The method of claim 18, wherein the fatty acid alkyl ester component is formed in the biorefinery via one or more enzymes chosen from lipase, esterase, and combinations thereof, wherein the one or more enzymes are exogenous enzymes.

21. A method of refining a grain oil composition to make one or more grain oil products, the method comprising:
 a) providing a grain oil composition obtained from a biorefinery, wherein the grain oil composition comprises a fatty acid alkyl ester component and a free fatty acid component, wherein the free fatty acid component is present in the grain oil composition in an amount in the range from 0.5 to 9 percent by weight based on the total weight of the grain oil composition; and
 b) exposing the grain oil composition to temperature and pressure conditions for a time period to evaporate at least a portion of the fatty acid alkyl ester component from the grain oil composition to form a first grain oil product and a second oil product, wherein the first grain oil product has a first concentration of fatty acid alkyl ester component and the second grain oil product has a second concentration of fatty acid alkyl ester component, and wherein the first concentration of fatty acid alkyl ester component is less than the second concentration of fatty acid alkyl ester component.

22. The method of claim 21, further comprising using the first grain oil product and/or the second grain oil product as a feedstock to make diesel.

23. The method of claim 21, wherein the fatty acid alkyl ester component is formed in the biorefinery via one or more enzymes chosen from lipase, esterase, and combinations thereof, wherein the one or more enzymes are endogenous enzymes and/or exogenous enzymes.

24. A defoamer comprising the first grain oil product of claim 21.

* * * * *